US008609878B2

(12) United States Patent
Fridag et al.

(10) Patent No.: US 8,609,878 B2
(45) Date of Patent: Dec. 17, 2013

(54) METHOD FOR PRODUCING 6-CHLORODIBENZO[D,F] [1 3,2]DIOXAPHOSPHEPIN

(75) Inventors: Dirk Fridag, Haltern am See (DE); Robert Franke, Marl (DE); Bernhard Schemmer, Haltern am See (DE); Burkard Kreidler, Recklinghausen (DE); Bjoern Wechsler, Borken (DE)

(73) Assignee: Evonik Oxeno GmbH, Marl (DE)

( * ) Notice: Subject to any disclaimer, the term of this patent is extended or adjusted under 35 U.S.C. 154(b) by 121 days.

(21) Appl. No.: 13/123,469

(22) PCT Filed: Oct. 9, 2009

(86) PCT No.: PCT/EP2009/063139
§ 371 (c)(1),
(2), (4) Date: Apr. 8, 2011

(87) PCT Pub. No.: WO2010/052090
PCT Pub. Date: May 14, 2010

(65) Prior Publication Data
US 2011/0201837 A1    Aug. 18, 2011

(30) Foreign Application Priority Data

Nov. 7, 2008    (DE) .......................... 10 2008 043 582

(51) Int. Cl.
*C07F 9/6571*    (2006.01)
(52) U.S. Cl.
USPC ......................................................... 558/84
(58) Field of Classification Search
None
See application file for complete search history.

(56) References Cited

U.S. PATENT DOCUMENTS

| 7,345,185 | B2 | 3/2008 | Ortmann et al. |
| 7,767,861 | B2 | 8/2010 | Ortmann et al. |
| 2009/0292146 | A1 | 11/2009 | Hess et al. |
| 2010/0137623 | A1 | 6/2010 | Selent et al. |

FOREIGN PATENT DOCUMENTS

| CN | 1 986 055 | 6/2007 |
| EP | 0432506 | * 11/1990 |
| WO | 2005 063776 | 7/2005 |
| WO | 2008 124468 | 10/2008 |
| WO | WO2010042313 | * 10/2008 |
| WO | 2009 120210 | 10/2009 |

OTHER PUBLICATIONS 2,2'-biphenol, 2013, sigma aldrich material safety data sheet.*
Abdou, W. et al. "Inhibition of Pseudorotation in some Monocyclic Pentaoxyphosphoranes." Phosphorus and Sulfur vol. 22 (Jan. 1, 1985) pp. 99-107. XP 8099059.
International Search Report issued Jan. 13, 2010 in PCT/EP2009/063139 filed Oct. 9, 2009.
U.S. Appl. No. 13/127,184, filed May 2, 2011, Fridag, et al.

* cited by examiner

*Primary Examiner* — Sun Jae Loewe
(74) *Attorney, Agent, or Firm* — Oblon, Spivak, McClelland, Maier & Neustadt, L.L.P.

(57) ABSTRACT

The invention relates to a method for producing 6-chlorodibenzo[d,f][1,3,2]-dioxaphosphepin (formula 1), comprising the following steps: a) addition of liquid 2,2'-dihydroxybiphenyl into a reactor to an excess of phosphorous trichloride under inert gas and stirring; b) discharge and neutralization of the resulting gases from the reaction mixture; c) separation of the excess phosphorous trichloride; d) obtention of 6-chlorodibenzo[d,f][1,3,2]-dioxaphosphepin.

11 Claims, No Drawings

METHOD FOR PRODUCING 6-CHLORODIBENZO[D,F] [1 3,2]DIOXAPHOSPHEPIN

The invention relates to a process for preparing 6 chlorodibenzo[d,f][1,3,2]dioxaphosphepin, compound 1.

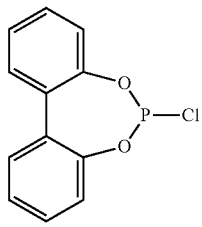

1

Compound 1 is a building block which plays an important role in, inter alia, the synthesis of ligands.

An example of such a ligand is the compound 2, 6,6'-[(3,3'-di-tert-butyl-5,5'-dimethoxy-1,1'-biphenyl-2,2'-diyl)bis(oxy)]bis(dibenzo[d,f][1,3,2]dioxaphosphepin), referred to as biphephos, which has found widespread use in transition metal-catalyzed reactions.

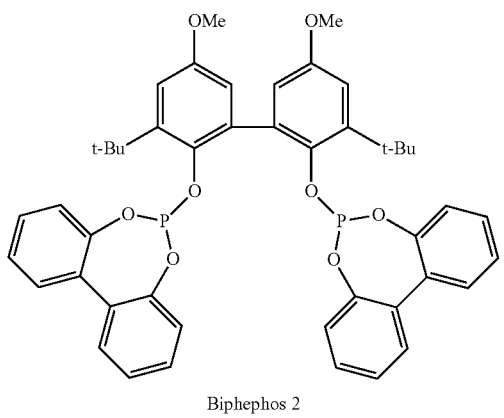 [SMILES: COc1cc(-c2cc(OC)cc(C(C)(C)C)c2Op2oc3ccccc3c3ccccc3o2)c(Op2oc3ccccc3c3ccccc3o2)c(C(C)(C)C)c1]

Biphephos 2

The compound 2 is used, for example, in the transition metal-catalyzed hydroaminomethylation (E. Petricci, A. Mann, J. Salvadori, M. Taddei, Tetrahedron Letters 2007, 48, 8501-8504), hydrocyanation (U.S. Pat. No. 5,449,807), hydroformylation (U.S. Pat. No. 4,769,498, CN1986055), isomerization (U.S. Pat. No. 5,440,067) and cyclohydrocarbonylation (U.S. Pat. No. 5,962,744) of olefins.

Compound 2 is usually prepared from commercially available starting materials in three synthesis steps: to produce the backbone, 3-tert-butyl-4-hydroxyanisole is oxidized to the biaryl compound 3,3'-tert-butyl-2,2'-dihydroxy-5,5'-dimethoxybiphenyl. To produce the side wings, phosphorus trichloride is reacted with 2,2'-dihydroxybiphenyl to form compound 1. Finally, the reaction products of the two steps mentioned are condensed with one another in the presence of a base to form compound 2, biphephos.

All processes known hitherto for preparing compound 1 (6-chlorodibenzo[d,f][1,3,2]dioxaphosphepin) lead to formation of undesirable by-products and thus a reduced yield or else require a high outlay in terms of energy or time.

Thus, in U.S. Pat. No. 4,769,498 phosphorus trichloride is added dropwise to 2,2'-dihydroxybiphenyl, forming phosphitic by-products which can be substantially suppressed only by energy-intensive thermal equilibration for a number of hours (cf. L. Anschutz, W. Marquardt, Chem. Ber. 1956, 89, 1119-1123) or/and a complicated vacuum distillation of the product has to be carried out, requiring either very high temperatures (ibid and in L. V. Verizhnikov and P. A. Kirpichnkov, Zh. Obshch. Khim., 1967, 37, 1355) or vacuums of 130 Pa and less which are difficult to realize industrially (EP 0 730 574 and V. N. Tsarev, A. A. Kabro, S. K. Moiseev, V. N. Kalinin, O. G. Bondarev, V. A. Davankov, K. N. Gavrilov, Russ. Chem. Bull., Int. Ed. Vol. 53, 2004, 814-818).

In CN1986055, on the other hand, an excess of phosphorus trichloride is placed in a reaction vessel and 2,2'-dihydroxybiphenyl is added thereto. However, further details regarding the manner of the addition, and also the reaction conditions for a compound which is as highly reactive toward phosphorus trichloride as 2,2'-dihydroxybiphenyl are not provided. Compound 1 is separated from the reaction mixture and purified further by means of vacuum distillation, but once again further details such as pressure and temperature range are absent. The yield of 1 is 71%. Closer characterization of 1 is not disclosed.

The analogous process disclosed in FR 2873696 requires energy-intensive cooling of the reaction mixture to 0° C. in order to obtain sufficient selectivity and the addition of an amine to scavenge the hydrogen chloride gas formed, with the consequence that an amine hydro-chloride which has to be filtered off is formed. However, since the entire reaction mixture is highly corrosive, it requires an expensive filtration apparatus (because it has to be corrosion resistant), for example a filtration apparatus made of DIN 2.4610 alloys. In addition, the amine hydrochloride waste formed has to be disposed of or recycled, which is expensive.

Furthermore, the authors have established that in the process in tetrahydrofuran described by A. van Rooy, P. C. J. Kamer, P. W. N. M. van Leeuwen, K. Goubitz, J. Fraanje, N. Veldman and A. L. Spek in Organometallics 1996, 15, 835-847, the addition of base described there is not permissible since otherwise up to 10% of by-products formed by acid cleavage of tetrahydrofuran could be formed. However, the necessary addition of an amine once again requires the expensive filtration and/or a vacuum distillation.

Furthermore, apart from the aspects product yield and purity, it is critical that the addition of the 2,2'-dihydroxybiphenyl is carried out in such a way that the removal of heat from this condensation reaction is carried out in a controlled way in order for the process of the invention to be carried out safely, especially with a view to implementation as an industrial process.

In Zh. Obshch. Khim., 1967, 37, 1355, L. V. Verizhnikov and P. A. Kirpichnkov report a process variant in which the starting materials phosphorus trichloride and 2,2'-dihydroxybiphenyl are mixed at room temperature, heated to boiling and the product is subsequently separated off by high-vacuum distillation.

Since two highly reactive compounds are mixed directly there, the criterion of controlled heat removal can no longer be guaranteed in the case of large batches. The heat of reaction is −54 kJ/mol and the reaction is therefore strongly exothermic. However, controlled heat removal is absolutely necessary on an industrial scale for safety reasons. Otherwise, the entire quantity of heat could be liberated suddenly on direct mixing of two highly reactive compounds. This quantity of heat can still be removed without danger in the case of small laboratory batches, but in the case of reactions on an industrial scale there is a considerable hazard potential.

It is therefore an object of the invention to develop a process which provides compound 1 from 2,2'-dihydroxybiphenyl and phosphorus trichloride in high yield and purity without making recourse to energy-intensive equilibration or cooling operations and makes do without product distillation, addition of base or use of tetrahydrofuran. In the ideal case, the process is free from solvent and can be managed safely on an industrial scale.

It has been found that this object can be achieved by introducing 2,2'-dihydroxybiphenyl in liquid form, preferably as a melt by means of a heatable starting material reservoir, heatable pump and line, into phosphorus trichloride. In particular, the addition is carried out under inert gas. Suitable inert gases are, for example, nitrogen and all noble gases (helium, neon, argon, krypton, xenon, radon), and preference is given to using nitrogen. The addition of 2,2'-dihydroxybiphenyl is particularly preferably carried out in a temperature range from 110 to 130° C. and a pressure range from 0.07 to 0.12 MPa. Controlling the inflow rate of liquid 2,2'-dihydroxybiphenyl into phosphorus trichloride ensures safe removal of the heat of reaction. The use of a base for scavenging the hydrogen chloride formed can be dispensed with. The hydrogen chloride gas formed is instead passed via a vapor line into, for example, a waste air scrubber filled with sodium hydroxide solution. After the reaction is complete, excess phosphorus trichloride is separated off, preferably by distillation, giving compound 1 in quantitative yield and purities greater than or equal to 98%. The phosphorus trichloride which has been separated off is recycled and used for a fresh reaction.

The invention is accordingly a process for preparing 6-chlorodibenzo[d,f][1,3,2]dioxaphosphepin, which comprises the following steps:
a) addition of liquid 2,2'-dihydroxybiphenyl to an excess of phosphorus trichloride under inert gas in a reactor and stirring;
b) discharge and neutralization of the resulting gases from the reaction mixture;
c) removal of the excess phosphorus trichloride, preferably after the end of the reaction;
d) isolation of 6-chlorodibenzo[d,f][1,3,2]dioxaphosphepin.

In particular, a 2- to 25-fold, preferably 10- to 15-fold, excess of phosphorus trichloride, based on molar ratios, is present here.

Even without further details, it is assumed that a person skilled in the art can utilize the above description in its widest scope. The preferred embodiments and examples are therefore to be interpreted merely as descriptive disclosures which do not limit the invention in any way. The present invention is illustrated below with the aid of examples. Alternative embodiments of the present invention can be obtained in an analogous way.

EXAMPLE 177.65 g (0.96 mol) of 2,2'-dihydroxybiphenyl were placed in a 1000 ml heatable starting material reservoir which had been made inert by means of nitrogen, heated to a temperature range from 110 to 130° C. in a pressure range from 0.08 to 0.12 MPa and melted. 1574 g (11.46 mol) of phosphorus trichloride were placed in a 6000 ml reactor which had been made inert by means of nitrogen and can be thermostated. The reactor was thermostated to 20° C., stirred and was connected via a waste air scrubber filled with sodium hydroxide solution to a membrane pump. A working pressure of from 0.07 to 0.09 MPa was set to ensure that gases formed were safely discharged via the waste air scrubber. The content of the starting material reservoir was pumped into the reactor over a period of 2.5 hours using a heatable pump. After the addition was complete, the mixture was stirred at 20° C. for 15 minutes, and a clear, slightly yellowish solution is obtained in the reactor. The reactor was subsequently evacuated to 0.02 MPa and thermostated at 50° C. Excess phosphorus trichloride was distilled off under a protective nitrogen atmosphere. During the distillation, the temperature was increased stepwise to 91° C. After 1.15 hours, the distillation was concluded and a colorless, highly viscous liquid remained.

Yield: >99% of theory. Purity: 98%; determined by GC/MS and $^{31}$P-NMR measurement (500 MHz high-field measurement using 85% orthophosphoric acid as external standard, 1 dissolved in d8-toluene) at a shift of δ=185.21 ppm.

The invention claimed is:

1. A process for preparing 6-chlorodibenzo-[d,f]-[1,3,2] dioxa-phosphepin, comprising:
   a) adding liquid 2,2'-dihydroxybiphenyl to an excess of phosphorus trichloride under an inert gas in a reactor to give a reaction mixture, and stirring the reaction mixture;
   b) discharging and neutralizing at least one gas obtained from the reaction mixture;
   c) removing excess phosphorus trichloride; and
   d) isolating the 6-chlorodibenzo[d,f][1,3,2]dioxaphosphepin.

2. The process as claimed in claim 1, wherein said liquid 2,2'-dihydroxybiphenyl is in a molten state when added and is carried out in a temperature range from 110 to 130° C. and in a pressure range from 0.07 to 0.12 MPa.

3. The process as claimed in claim 1, wherein the excess phosphorus trichloride which is separated off in the removing is recirculated to the process.

4. The process as claimed in claim 1, wherein a 2- to 25-fold excess of phosphorus trichloride is present in the adding.

5. The process as claimed in claim 2, wherein the excess phosphorus trichloride which is separated off in the removing is recirculated to the process.

6. The process as claimed in claim 2, wherein a 2- to 25-fold excess of phosphorus trichloride is present in the adding.

7. The process as claimed in claim 3, wherein a 2- to 25-fold excess of phosphorus trichloride is present in the adding.

8. The process as claimed in claim 1, wherein a 10- to 15-fold excess of phosphorus trichloride is present in the adding.

9. The process as claimed in claim 2, wherein a 10- to 15-fold excess of phosphorus trichloride is present in the adding.

10. The process as claimed in claim 3, wherein a 10- to 15-fold excess of phosphorus trichloride is present in the adding.

11. The process according to claim 1, wherein said process is conducted free from solvent.

* * * * *